US012681026B2

(12) United States Patent
Huang et al.

(10) Patent No.: US 12,681,026 B2
(45) Date of Patent: Jul. 14, 2026

(54) QUANTITATIVE POOLED-SAMPLE TESTING METHOD AND APPARATUS FOR CHEMICAL TEST ITEMS OF CONSUMER PRODUCT

(71) Applicants: Shenzhen Technology University, Shenzhen (CN); Technology Center of Guangzhou Customs, Guangzhou (CN)

(72) Inventors: Lina Huang, Shenzhen (CN); Lezhou Yi, Guangzhou (CN); Xiaoxia Mai, Guangzhou (CN); Weiqiang Huo, Guangzhou (CN); Qing Zhang, Guangzhou (CN)

(73) Assignees: SHENZHEN TECHNOLOGY UNIVERSITY, Shenzhen (CN); TECHNOLOGY CENTER OF GUANGZHOU CUSTOMS, Guangzhou (CN)

( * ) Notice: Subject to any disclaimer, the term of this patent is extended or adjusted under 35 U.S.C. 154(b) by 882 days.

(21) Appl. No.: 18/274,719

(22) PCT Filed: Apr. 10, 2020

(86) PCT No.: PCT/CN2020/084096
§ 371 (c)(1),
(2) Date: Jul. 28, 2023

(87) PCT Pub. No.: WO2021/098128
PCT Pub. Date: May 27, 2021

(65) Prior Publication Data
US 2024/0118296 A1 Apr. 11, 2024

(30) Foreign Application Priority Data
Nov. 18, 2019 (CN) .......................... 201911128397.1

(51) Int. Cl.
*G01N 35/00* (2006.01)
*G16C 20/00* (2019.01)
*G16C 60/00* (2019.01)

(52) U.S. Cl.
CPC ....... *G01N 35/00584* (2013.01); *G16C 20/00* (2019.02); *G16C 60/00* (2019.02)

(58) Field of Classification Search
CPC .......................... G01N 35/00584; G16C 20/00
See application file for complete search history.

(56) References Cited

U.S. PATENT DOCUMENTS

| 10,392,598 | B2 | 8/2019 | Xu et al. | |
| 2007/0065803 | A1* | 3/2007 | Jurdic ................ | G01N 33/5017 |
| | | | | 435/325 |

(Continued)

FOREIGN PATENT DOCUMENTS

| CN | 104569314 A | 4/2015 |
| CN | 107132302 A | 9/2017 |

(Continued)

OTHER PUBLICATIONS

Yi Lezhou, Test Model and Application of Consumer Goods in Chemical Analysis Hybrid, Journal of Inspection and Quarantine, 2019, pp. 20-24, vol. 29, No. 4.

(Continued)

*Primary Examiner* — Catherine T. Rastovski
*Assistant Examiner* — Sharah Zaab
(74) *Attorney, Agent, or Firm* — Bayramoglu Law Offices LLC

(57) ABSTRACT
A quantitative pooled-sample testing method and apparatus for chemical test items of consumer products are provided. The test method includes: calculating a maximum number of samples that can be pooled according to parameters such as regulatory limit requirements, measurement uncertainty, the (Continued)

number of pooled samples, a sample pooling ratio, and the like; establishing a searchable table according to a relationship between a qualified rate, the number of samples that can be pooled, and reduced workload; for various items to be tested, directly querying the table to acquire reduced workloads corresponding to different numbers of samples that can be pooled; and when the number of samples that can be pooled does not exceed a maximum value and corresponds to the most greatly reduced workload, determining that number of samples that can be pooled as an optimum number of samples that can be pooled, and performing pooled-sample testing.

12 Claims, 4 Drawing Sheets

(56) References Cited

U.S. PATENT DOCUMENTS

| | | | | |
|---|---|---|---|---|
| 2012/0059599 A1* | 3/2012 | Cunningham | ......... | G16C 20/64 |
| | | | | 703/11 |
| 2014/0357504 A1* | 12/2014 | Trau | ..................... | G01N 33/543 |
| | | | | 506/18 |

FOREIGN PATENT DOCUMENTS

| | | | | | |
|---|---|---|---|---|---|
| CN | 107506333 | A | 12/2017 | | |
| CN | 108037089 | A | 5/2018 | | |
| CN | 108459126 | * | 8/2018 | ............. | G01N 30/86 |
| CN | 108459126 | A | 8/2018 | | |
| CN | 109061125 | * | 8/2018 | ............. | G01N 33/48 |
| CN | 109060396 | A | 12/2018 | | |
| CN | 109061125 | A | 12/2018 | | |
| CN | 109060396 | * | 8/2019 | .......... | G01M 99/008 |
| CN | 110411958 | A | 11/2019 | | |
| CN | 110907599 | A | 3/2020 | | |
| JP | 2007316017 | A | 12/2007 | | |
| WO | 2019168391 | A1 | 9/2019 | | |

OTHER PUBLICATIONS

Retrieved From: "https://baike.baidu.com/item/standarduncertainty?fromModule=lemma_search-box".

GB/T 22048-2015, Determination of certain phthalate esters in toys and children's products, (ISO 8124-6: 2014 Safety of toys—Part 6: Certain phthalate esters in toys and children's products, MOD), 2015, pp. 1-22.

ISO 8124-6, Safety of toys—Part 6: Certain phthalate esters in toys and children's products, International Standard, 2018, pp. 1-32.

ISO 14362-1, Textiles—Methods for determination of certain aromatic amines derived from azo colorants—Part 1 Detection of the use of certain azo colorants accessible with and without extracting the fibres, 2017, pp. 1-32.

GB 6675.1-2014, Toys safety—Part 1: Basic code, 2014, pp. 1-10.

Testing Methods: Standard 100 by Oeko Tex®, International Association for Research and Testing in the Field of Textile and Leather Ecology, 2018, pp. 1-9.

ISO/TC 181-N 1156, Safety of toys, 2019, pp. 1-33.

Testing and evaluation of polycyclics aromatic hydrocarbons (PAK) when awarding the GS mark, 2014, pp. 1-13, Federal Institute for Occupational Safety and Health.

Robert Dorfman, The Detection of Defective Members of Large Populations, pp. 436-440.

* cited by examiner

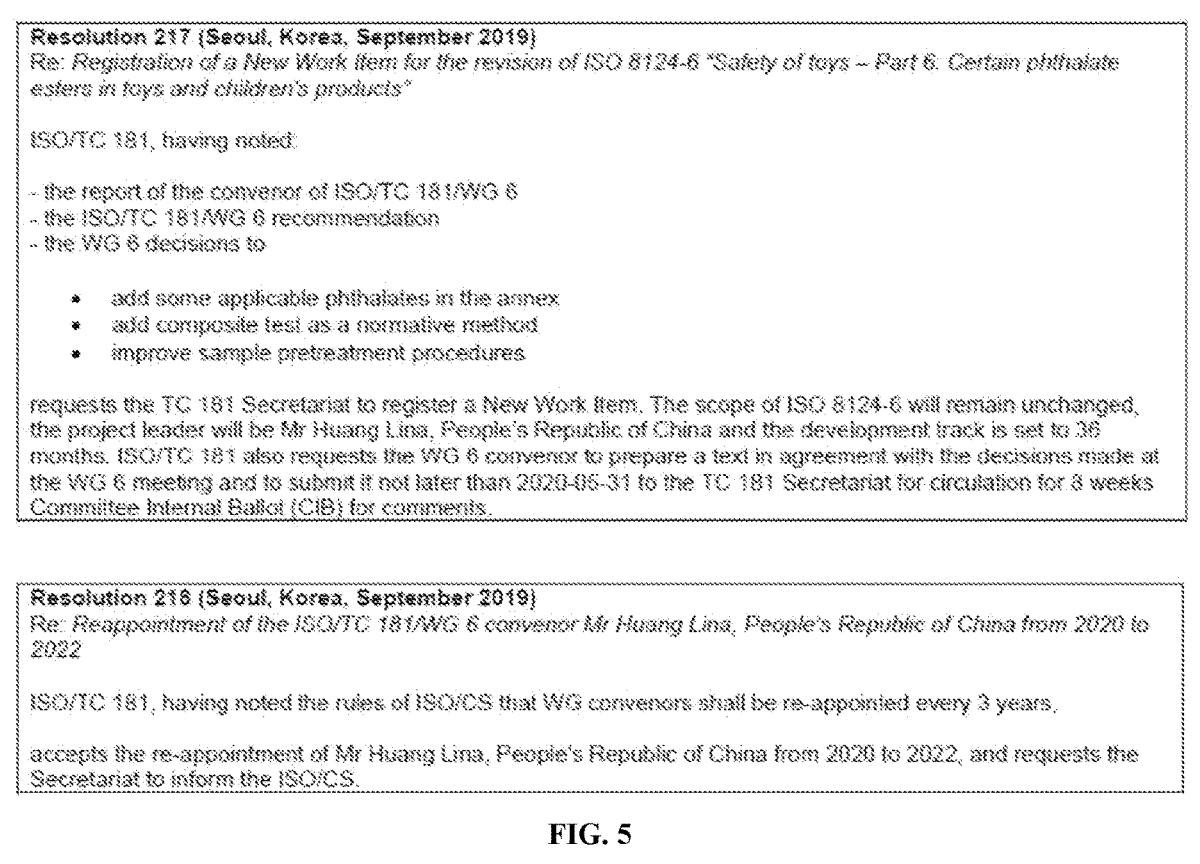

Resolution 217 (Seoul, Korea, September 2019)
Re: *Registration of a New Work Item for the revision of ISO 8124-6 "Safety of toys – Part 6. Certain phthalate esters in toys and children's products"*

ISO/TC 181, having noted:

- the report of the convenor of ISO/TC 181/WG 6
- the ISO/TC 181/WG 6 recommendation
- the WG 6 decisions to

* add some applicable phthalates in the annex
  * add composite test as a normative method
  * improve sample pretreatment procedures requests the TC 181 Secretariat to register a New Work Item. The scope of ISO 8124-6 will remain unchanged, the project leader will be Mr Huang Lina, People's Republic of China and the development track is set to 36 months. ISO/TC 181 also requests the WG 6 convenor to prepare a text in agreement with the decisions made at the WG 6 meeting and to submit it not later than 2020-05-31 to the TC 181 Secretariat for circulation for 8 weeks Committee Internal Ballot (CIB) for comments.

---

Resolution 216 (Seoul, Korea, September 2019)
Re: *Reappointment of the ISO/TC 181/WG 6 convenor Mr Huang Lina, People's Republic of China from 2020 to 2022*

ISO/TC 181, having noted the rules of ISO/CS that WG convenors shall be re-appointed every 3 years, accepts the re-appointment of Mr Huang Lina, People's Republic of China from 2020 to 2022, and requests the Secretariat to inform the ISO/CS.

FIG. 5

QUANTITATIVE POOLED-SAMPLE TESTING METHOD AND APPARATUS FOR CHEMICAL TEST ITEMS OF CONSUMER PRODUCT

CROSS REFERENCE TO THE RELATED APPLICATIONS

This application is the national phase entry of International Application No. PCT/CN2020/084096, filed on Apr. 10, 2020, which is based upon and claims priority to Chinese Patent Application No. 201911128397.1 filed on Nov. 18, 2019. the entire contents of which are incorporated herein by reference.

TECHNICAL FIELD

The present invention relates to the field of chemical testing technologies, and in particular to a quantitative pooled-sample testing method and apparatus for chemical test items of a consumer product.

BACKGROUND

With the rising in people's living standards, there are increasing varieties of consumer products with increasing functions, which thus causes chemical risks in the use of consumer products to be gradually more prominent. For example, the content of formaldehyde and banned azo colorants in textiles may exceed the standard, the heavy metals in leather products may exceed the standard, and plasticizers in toy products may exceed the standard. It is duty-bound for manufacturers and quality inspection and certification organizations to carry out safety testing of the consumer products and thus ensure the safety and health of consumers. With the spread of the "Belt and Road" project, the development of economic globalization and the increasing in willingness to test, the testing industry has continued to grow at a rapid pace. The global testing industry market reaches $1,225.7 billion in 2015, of which consumer products account for 9% of the share and is expected to maintain an average annual growth rate of 5%-7% in the next few years. The market size of China's testing industry is also growing rapidly, having reached 257.4 billion yuan in 2015. In addition, for many manufacturers, quality testing before the product leaves the factory is an effective means to detect unqualified products, which helps to ensure the quality of products. In terms of environmental protection, due to a large number of testing organizations, the environmental pollution as caused by the emission of pollutant gases during the testing process and the health concerns to experimenters as caused by the reagents used in the testing process are all major practical problems. In terms of economic benefits for testing organizations, a high cost is caused as the testing of consumer products involves a wide variety of samples, complex testing items, long testing cycles, a heavy workload for testing persons and reagent recycling and processing. Therefore, under the premise of ensuring good quality, it is a top priority for the country and quality inspection and certification organizations to optimize the inspection process, improve the testing efficiency, reduce the pollution emissions, and thus promote the healthy development of the industry with the concept of "faster, better, greener".

If each batch of samples is tested, a lot of labor, materials and money are required and environmental friendliness cannot be achieved. In addition, according to statistics, the positive detection rate of most test items is less than 1%.

Therefore, it is important to choose a simple, easy and scientifically effective screening method. At this point, the pool testing method emerges. The pool testing method is that several samples are combined into a group, in case that it needs to determine whether the items to be tested of a single sample are negative or qualified, when the items to be tested in this pooled sample are negative or qualified (regarded as a single sample), the items to be tested in the samples that are pooled are all given a negative or qualified result and only one test is needed; and when the items to be tested in the pooled sample are positive or unqualified (regarded as a single sample), each sample in the pooled sample is tested one by one. According to the pooled-sample testing method, firstly, it is possible to reduce the number of tests during the testing analysis, and the most fundamental benefit lies in the capacity to reduce the workload, improve the work efficiency and greatly reduce the testing cost, thereby achieving significant economic and social benefits. Secondly, the pooled-sample testing can reduce the use of solvents and reagents, thereby reducing the environmental pollution and the impact on the health of experimenters.

As early as 1943, Dorfman employed the pooled-sample testing method in infectious disease research: he combined several sera into one group, if the group was given a negative result, it requires only one test; and if the result was positive, each serum would be tested separately. As a result, the testing efficiency was improved greatly, but the testing sensitivity was reduced. Currently, the report of pool testing has occurred in different industries, such as the fields of epidemiology, DNA testing, entomology, food and consumer products. Specifically, in the field of consumer products, requirements for pool testing are merely mentioned in Standard for Testing Plasticizers in Toys and Children's Products GB/T 22048-2015, ISO 8124-6:2018 and Standard for Testing Azo Colorants in Textiles ISO 14362-1:2017. In addition, only similar materials, but not different types of materials can be subjected to pool testing because the pooled sample tests lack scientific modeling. Therefore, the testing is carried out in a more conservative way, and the pool testing is only used for qualitative screening and cannot be used for accurate quantification, thereby failing to achieve the maximum efficiency of screening.

Therefore, which test items suitable for pool testing and how to determine the maximum number for the pool testing are core issues requiring further investigation. The key to the sample pooling method is how to determine the size of a pooled sample, that is, how many samples are combined as a pooled sample to be tested and how many such pooled samples should be tested to meet certain accuracy requirements, which is known as the number of pooled samples or the number of tests. The pool testing method, when not applied properly, may not only fail to save the time and cost but also directly affect the accuracy of the testing results. The present invention proposes for the first time to introduce the uncertainty into a pooled-sample testing model, and on the basis of selecting representative products and test items and the application of probability theory, mathematical statistics and other theories and in combination with rigorous statistical analysis of more than 100,000 samples, refines a quantitative pooled-sample testing model that can be applied to test items in the field of consumer products and has scientific basis, operability and practicality.

SUMMARY

Based on this, it is necessary to provide a quantitative pooled-sample testing method and apparatus for chemical test items of consumer products to balance the contradiction between the workload and the accuracy of testing results. Different from the existing qualitative screening methods, the present invention innovatively introduces a combined uncertainty and an expanded uncertainty of the testing method into the pool testing model, clearly determines the optimum number of samples that can be pooled, and forms a scientific quantitative pooled-sample testing model. To achieve the object above, the present invention adopts following technical solutions.

A quantitative pooled-sample testing method for chemical test items of consumer products, including the steps of:

Acquiring relevant data of an item to be tested, and entering the relevant data into a following model to calculate the maximum number of samples that can be pooled:

$$K_{max} = L \times (1 - U_{rel}) \times F \times \frac{m_{tot}}{V} \div IDL \div M,$$

Where $K_{max}$ refers to the maximum number of samples that can be pooled, which is rounded by removing the mantissa; L refers to a quantity limit or report limit of the item to be tested and is in mg/kg; $U_{rel}$ refers to a relative expanded uncertainty around a limit concentration; F refers to a safety factor of the quantity limit or report limit; $m_{tot}$ refers to a total mass of samples subjected to pool testing and is in g; V refers to a volume of a volume-metered solution and is in mL; IDL refers to an instrument detection limit and is in mg/L; M refers to a number of the items to be tested corresponding to the quantity limit or report limit;

If the quantity limit is only one chemical test item, calculating the $U_{rel}$ which is the relative expanded uncertainty around the limit concentration, according to following formulas:

$$U_{rel} = u_{rel} \times k$$

$$u = \sqrt{u_{rel,1}^2 + u_{rel,2}^2 + u_{rel,3}^2},$$

Where $u_{rel}$ refers to a relative standard uncertainty around the limit concentration; k refers to a coverage factor taken with a confidence level of 95%, and k=2; $u_{rel,1}$ refers to a relative standard uncertainty of method reproducibility, which is namely a standard deviation of reproducibility data; $U_{rel,2}$ refers to a relative standard uncertainty of a method recovery rate; and $U_{rel,3}$ refers to a relative standard uncertainty of a standard curve, which is namely a standard deviation of reproducibility data;

If the quantity limit is a sum of multiple chemical test items, calculating the $U_{rel}$ which is the relative expanded uncertainty around the limit concentration, according to following formulas:

$$U_{rel} = u \div L \times k$$

$$u = \sqrt{u_1^2 + u_2^2 + u_3^2 + \ldots + u_n^2},$$

Where u refers to a standard uncertainty around the limit concentration and is in mg/L; L refers to the quantity limit or report limit of the item to be tested and is in mg/kg; k refers to the coverage factor taken with the confidence level of 95% and k=2; $u_1$ refers to a standard uncertainty of an item 1 to be tested and is in mg/kg; $u_2$ refers to a standard uncertainty of an item 2 to be tested and is in mg/kg; and $u_3$ refers to a standard uncertainty of an item 3 to be tested and is in mg/kg;

Determining a positive rate or unqualified rate of the item to be tested, querying a workload-reducing efficiency table to selecting a number of samples that can be pooled, which reduces workload most greatly, among 2 to $K_{max}$ as an optimum number of samples that can be pooled, where the workload-reducing efficiency table is established according to the following formula:

$$S = q^K - \frac{1}{K},$$

Where S refers to reduced workload, q refers to the positive rate or unqualified rate, and K refers to the number of samples that can be pooled; and Grouping samples to be tested according to the optimum number of samples that can be pooled, and performing pooled-sample testing.

Preferably, after the pooled-sample testing, a maximum content of a substance to be tested in a single test sample is calculated; and if the maximum content exceeds a corrected quantity limit or report limit, the pooled sample is split and then the samples are tested separately.

Preferably, the positive rate/unqualified rate of the items to be tested is less than 20%.

Preferably, the safety factor F of the quantity limit or report limit ranges from 0% to 100%.

A quantitative pooled-sample testing apparatus for chemical test items of consumer products, including:

A module for calculating a maximum number of samples that can be pooled, configured to: acquire relevant data of an item to be tested, and enter the relevant data into the following model to calculate the maximum number of samples that can be pooled:

$$K_{max} = L \times (1 - U_{rel}) \times F \times \frac{m_{tot}}{V} \div IDL \div M,$$

Where $K_{max}$ refers to the maximum number of samples that can be pooled, which is rounded by removing the mantissa; L refers to a quantity limit or report limit of the item to be tested and is in mg/kg; $U_{rel}$ refers to a relative expanded uncertainty around a limit concentration; F refers to a safety factor of the quantity limit or report limit; $m_{tot}$ refers to a total mass of samples subjected to pool testing and is in g; V refers to a volume of a volume-metered solution and is in mL; IDL refers to an instrument detection limit and is in mg/L; M refers to a number of the items to be tested corresponding to the quantity limit or report limit;

If the quantity limit is only one chemical test item, the $U_{rel}$ which is the relative expanded uncertainty around the limit concentration is calculated according to the following formulas:

$$U_{rel} = u_{rel} \times k$$

$$u = \sqrt{u_{rel,1}^2 + u_{rel,2}^2 + u_{rel,3}^2},$$

Where $u_{rel}$ refers to a relative standard uncertainty around the limit concentration; k refers to a coverage factor taken with a confidence level of 95% and k=2; $u_{rel,1}$ refers to a relative standard uncertainty of method reproducibility, which is namely a standard deviation of reproducibility data; $u_{rel,2}$ refers to a relative standard uncertainty of a method recovery rate; and $u_{rel,3}$ refers to a relative standard uncertainty of a standard curve, which is namely a standard deviation of reproducibility data;

If the quantity limit is a sum of multiple chemical test items, the $U_{rel}$ which is the relative expanded uncertainty around the limit concentration is calculated according to the following formulas:

$$U_{rel} = u \div L \times k$$

$$u = \sqrt{u_1^2 + u_2^2 + u_3^2 + \ldots + u_n^2},$$

Where u refers to a standard uncertainty around the limit concentration and is in mg/L; L refers to the quantity limit or report limit of the item to be tested and is in mg/kg; k refers to the coverage factor taken with the confidence level of 95% and k=2; $u_1$ refers to a standard uncertainty of an item 1 to be tested and is in mg/kg; $u_2$ refers to a standard uncertainty of an item 2 to be tested and is in mg/kg; and $u_3$ refers to a standard uncertainty of an item 3 to be tested and is in mg/kg;

A module for determining an optimum number of samples that can be pooled, configured to: according to a positive rate or unqualified rate of the item to be tested, query a workload-reducing efficiency table to select a number of samples that can be pooled, which reduces workload mostly greatly, among 2 to $K_{max}$ as the optimum number of samples that can be pooled, where the workload-reducing efficiency table is established according to the following formula:

$$S = q^K - \frac{1}{K},$$

Where S refers to reduced workload, q refers to the positive rate or unqualified rate, and K refers to the number of samples that can be pooled; and A pooled-sample testing module, configured to group samples to be tested based on the optimum number of samples that can be pooled and perform pooled-sample testing.

Preferably, after performing the pooled-sample testing, the pooled-sample testing module calculates a maximum content of a substance to be tested in a single test sample, and if the maximum content exceeds a corrected quantity limit or report limit, splits the pooled sample and the tests the samples separately.

Preferably, the positive rate/unqualified rate of the items to be tested is less than 20%.

Preferably, the safety factor F of the quantity limit or report limit ranges from 0% to 100%.

According to the present invention, the maximum number of samples that can be pooled, which can ensure the accuracy of testing results is calculated according to parameters such as regulatory limit requirements, measurement uncertainty, the number of pooled samples and the sample pooling ratio; then, a searchable table is established according to a relationship between the qualified rate, the number of samples that can be pooled and the reduced workload; for various items to be tested, the reduced workloads under different numbers of samples that can be pooled can be acquired directly querying the table; when the number of samples that can be pooled does not exceed the maximum value, and corresponds to the most greatly reduced workload, this number of samples that can be pooled is deemed as the optimum number of samples that can be pooled; and the pooled-sample testing is performed according to said number of samples that can be pooled. This can not only reduce the workload and improve the testing efficiency, but also can acquire a reliable testing result.

BRIEF DESCRIPTION OF THE DRAWINGS

FIG. 5 is a diagram for content of Resolutions 217 and 218 on "Safety of toys" issued by ISO/TC181 in 2019.

DETAILED DESCRIPTION OF THE EMBODIMENTS

Figure 1:
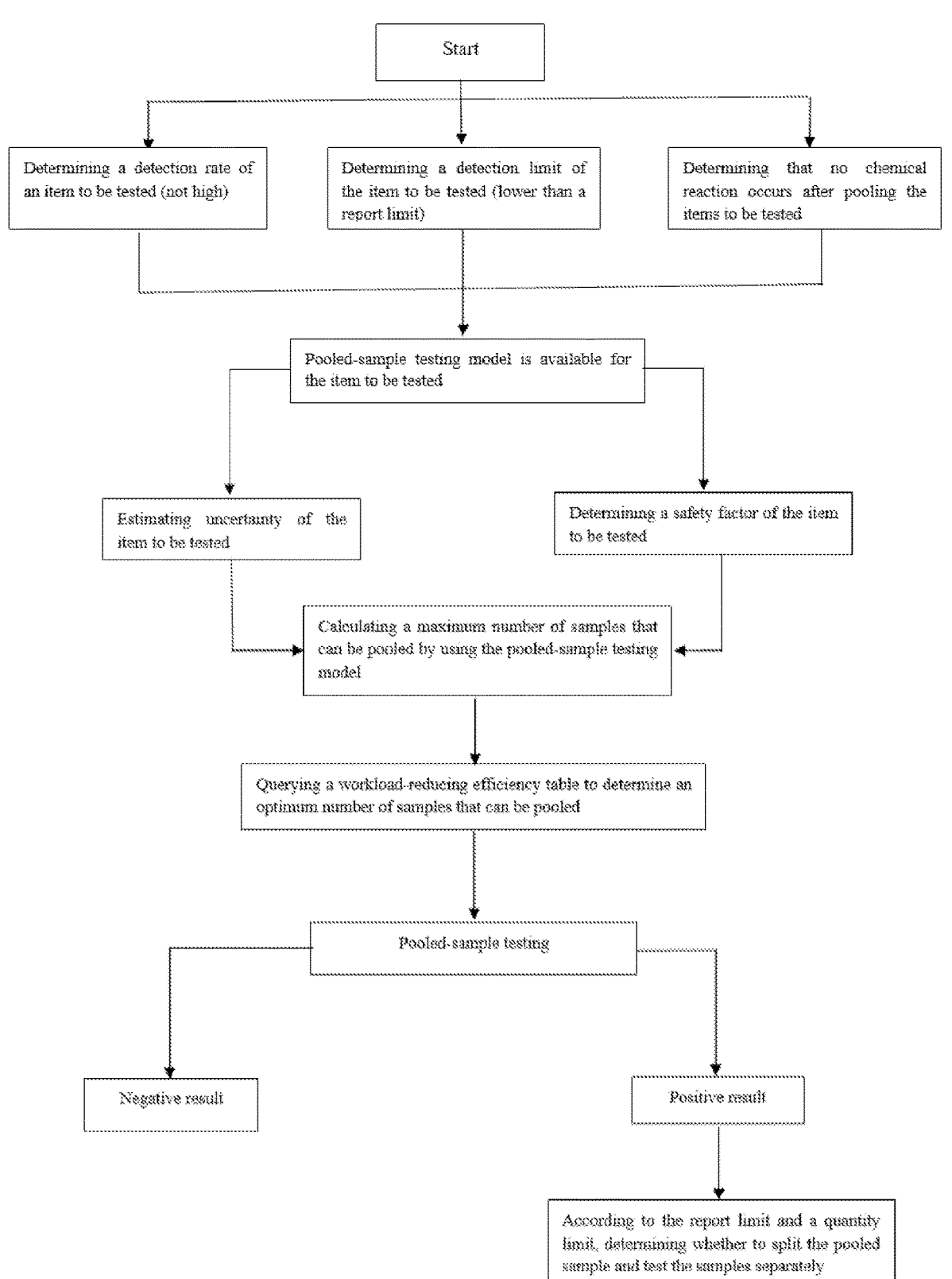
FIG. 1 is a schematic flowchart of a pooled-sample testing method for chemical test items of a consumer product according the present invention.

The present invention intends to establish a pooled-sample testing method and apparatus for pooled-sample testing technologies of consumer products, which will give optimum and maximum numbers of pooled samples and a risk threshold for the pooled-sample testing under different conditions. The method and apparatus are suitable for the calculation of the maximum number of samples that can be pooled in the pool testing of consumer products.

The current testing organizations, for cost-saving considerations, have a great demand for the pooled-sample testing. However, the determination of the maximum number for the pool testing is mostly ungrounded and largely relies on a simple addition of instrument detection limits, standard detection limits and inspection experience values, which lacks scientific basis and accuracy. On the basis of selecting representative products and tests, by taking into account a series of parameters such as regulatory limit requirements, sample uniformity, method detection limits, linearity range, measurement uncertainty, the number of pooled samples, sample pooling ratio, and physicochemical changes during the sample pooling process, on the basis of application of probability theory, mathematical statistics and other theories and in combination with rigorous statistical analysis of more than 100,000 samples collected from a wide range of testing organizations, the present invention refines a mathematical model that can be applied to test items in the field of consumer products and has scientific basis, operability and practicality.

Establishment of Mathematical Model to Determine the Number of Samples that Can be Pooled for Pool Testing 1) Workload Analysis If the positive or unqualified probability of certain item of a certain type of product is p, the corresponding negative or qualified probability is: q=1−p. Due to independence of events, the probability that K samples which are pooled are negative or qualified is $q^K$, and in this case only one test will be conducted; and the probability that K samples which are pooled are positive or unqualified is $1-q^K$, and in this case the K samples shall be tested one by one, requiring a total of K+1 tests. If the total number of samples is n, the total number N of tests after grouping is shown in formula (1) and table 1:

$$N = 1 \times q^K \times \frac{n}{K} + (K+1) \times (1-q^K) \times \frac{n}{K} = n\left(1 - q^K + \frac{1}{K}\right) < n, \quad (1)$$

where
N refers to the total number of tests;
q refers to the negative or qualified probability for certain item of a certain type of product;
K refers to the number of samples that can be pooled; and
n refers to the total number of samples.

TABLE 1

| Probability distribution | | | |
|---|---|---|---|
| Total number n of samples Pooling K samples per group Testing results | Number of tests | Probability | Total number of tests |
| Negative or qualified | 1 | $q^K$ | $1 \times q^E \times \frac{n}{K}$ |
| Positive or unqualified | K + 1 | $1 - q^K$ | $(K+1) \times (1-q^K) \times \frac{n}{K}$ |

Obviously, the purposes of reducing workload and improving efficiency can only be achieved when the total number N of tests after the grouping by pooling is less than the total number n of samples. Refer to formulas (2) and (3):

$$N = n\left(1 - q^K + \frac{1}{K}\right) < n, \quad (2)$$

and $$\text{reduced workload } S = q^K - \frac{1}{K} > 0. \quad (3)$$

In addition, in the case that the negative or qualified probability q is fixed, when the value of the reduced workload S reaches the maximum as the number K of samples that can be pooled varies, the corresponding value K at this point is the number of samples that can be pooled, theoretically having the optimum efficiency.

2) Analysis of Maximum Number of Samples that can be Pooled

Considering the screening accuracy of the pool testing scheme, some simple statistical analysis from the mathematical point of view may lead to a wrong conclusion that the pooled samples containing positive or unqualified samples are wrongly detected for example as being negative or qualified in the first test. Therefore, when determining the size of the pooled sample, it is important not only to maximize benefits and efficiency, but also to conduct a comprehensive analysis on the factors that affect the accuracy of the results. For example, the type, limits, materials, dilution ratios, method detection limits and the like of test items are all influential factors. In addition, because of the uncertainty of the pool testing, the selection of a safety factor is also necessary.

a. A formula for determining the size $K_{max}$ of the pooled sample to ensure the acquisition of a correct testing conclusion is acquired, referring to formula (4):

$$K_{max} = L \times (1 - U_{rel}) \times F \times \frac{m_{tot}}{V} \div IDL \div M, \quad (4)$$

where
$K_{max}$ refers to the maximum number of samples that can be pooled, being a value rounded by removing the mantissa;
L refers to the quantity limit/report limit of the test item in mg/kg, being a value selected according to the requirements of different standards and regulations or customer requirements; and
$U_{rel}$ refers to the relative expanded uncertainty around the limit concentration, where uncertainty which characterizes the dispersion of values reasonably attributed to the measurand and is associated with the measurement result is called measurement uncertainty. The expanded uncertainty is a quantity that defines the interval of the measurement result that may be expected to encompass a large fraction of the distribution of values reasonably attributed to the measurand. The expanded uncertainty is expressed by a multiple of combined standard uncertainty.

Due to the fact that the mathematical models of certain chemical item of the consumer product mostly involve multiplication, if the quantity limit is only one chemical item, the $U_{rel}$ which is the relative expanded uncertainty around the limit concentration, is calculated according to the following formulas:

$$U_{rel} = u_{rel} \times k$$

$$u = \sqrt{u_{rel,1}^2 + u_{rel,2}^2 + u_{rel,3}^2},$$

Where $u_{rel}$ refers to relative standard uncertainty around the limit concentration; k refers to a coverage factor taken with a confidence level of 95%, and k=2; $u_{rel,1}$ refers to relative standard uncertainty of method reproducibility, which is namely a standard deviation of reproducibility data; $u_{rel,2}$ refers to a relative standard uncertainty of a method recovery rate; and $u_{rel,3}$ refers to relative standard uncertainty of a standard curve, which is namely a standard deviation of reproducibility data. All of them can be adopted for uncertainty estimation of either category A or category B.

If the quantity limit is a sum of multiple chemical items, the $U_{rel}$ which is the relative expanded uncertainty around the limit concentration is calculated according to following formulas:

$$U_{rel} = u \div L \times k$$

$$u = \sqrt{u_1^2 + u_2^2 + u_3^2 + \dots + u_n^2},$$

Where $U_{rel}$ refers to the relative expanded uncertainty of testing result data around the limit concentration; u refers to standard uncertainty around the limit concentration and is in mg/L; L refers to the quantity limit or report limit of the item to be tested and is in mg/kg; k refers to the coverage factor taken with the confidence level of 95%, and k=2; $u_1$ refers to standard uncertainty of an item 1 to be tested and is in mg/kg; $u_2$ refers to standard uncertainty of an item 2 to be tested and is in mg/kg; and $u_3$ refers to standard uncertainty of an item 3 to be tested and is in mg/kg.

The quantity limit for test items of consumer products generally involves the sum of the content of respective detected substances. For example, in toy products, the sum of the content of three phthalate esters should not exceed 0.1%, and the sum of the content of 18 PAHs cannot exceed 1 mg/kg. Therefore, if the quantity limit is the sum of the respective detected substances, $U_{rel}$ is calculated according to the following formulas (5) and (6):

$$u(y) = \sqrt{u(a)^2 + u(b)^2 + \ldots}, \qquad (5)$$

Where u(a), u(b), . . . refer to the standard uncertainty components for respective detected substances respectively; and u(y) refers to the combined standard uncertainty of the sum of respective detected substances; and $$U_{rel} = \frac{u(y) \times 2}{L} \times 100\%. \qquad (6)$$

Note: the processing principle of subtraction is the same as that of addition.

F refers to the safety factor of the quantity limit/report limit. Due to the difference in testing capabilities and the diversity in materials, each laboratory can select a suitable safety factor based on experience and historical data, and the generally recommended value range is 0%-100%;

$m_{tot}$ refers to the total mass of samples subjected to pool testing in g;

V refers to the volume of a volume-metered solution in mL;

IDL refers to the instrument detection limit in mg/L; and

M refers to the number of test items corresponding to the quantity limit/report limit. For example, if certain quantity limit is the sum of three test items, M equals to 3.

Figure 3:
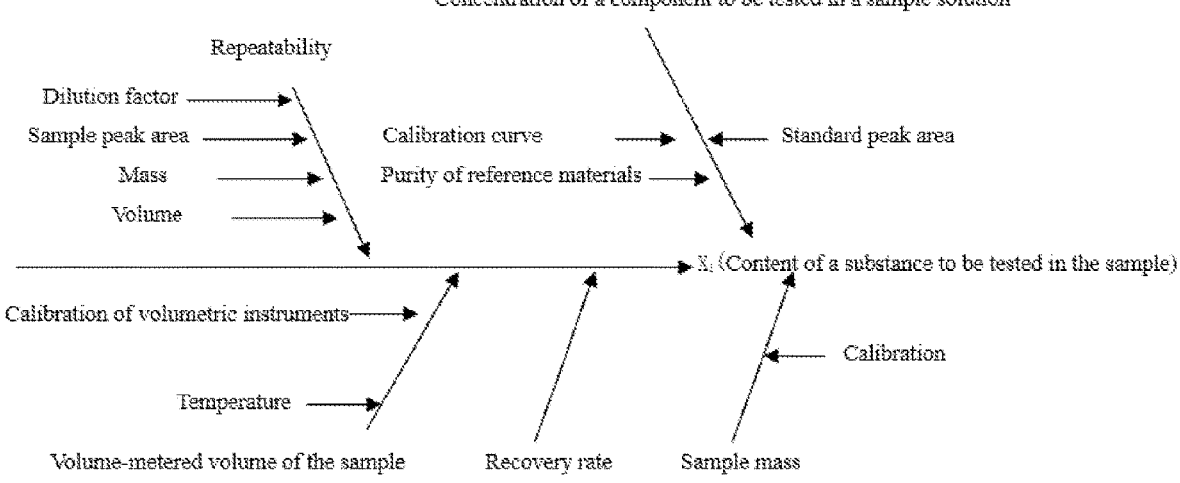
FIG. 3 is a causality diagram adopted for a quantitative analysis of uncertainty components.
Figure 4:
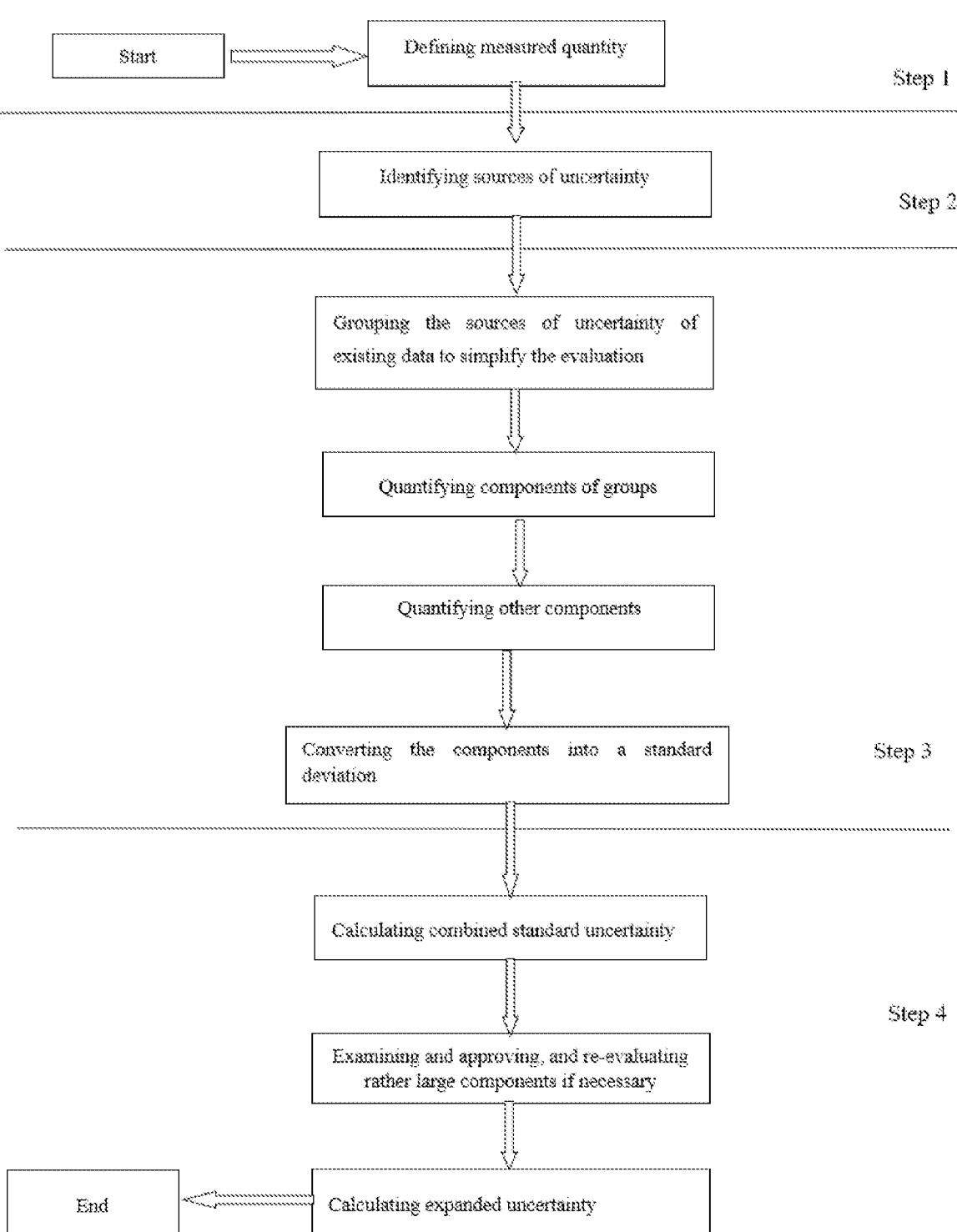
FIG. 4 is a schematic diagram of a process for evaluating relative expanded uncertainty according the present invention.

According to the formulas, the accuracy of the pool testing results is ensured under the considerations of the method detection limit, and the maximum value $K_{max}$ of the number of samples that can be pooled is acquired.

b. Evaluation of $U_{rel}$ which is the relative expanded uncertainty around the limit concentration, which as shown in FIG. 4 consists of the following steps:

step 1: defining the measured quantity;

step 2: identifying the source of uncertainty;

step 3: quantifying the uncertainty components, which can generally be analyzed by a causality diagram as shown in FIG. 3; and step 4: calculating the relative expanded uncertainty according to formula (5) and formula (6).

Procedure for Pooled-Sample Testing

1. Firstly, whether the pooled-sample testing can be conducted is determined according to the following conditions.

(1) The pooled sample is tested as possible as only once, which requires no splitting and retesting and thus reduces the total number of tests.

(2) The positive or unqualified rate of the items to be tested should be low, and may for example be less than 20%.

(3) After the samples to be tested are pooled, if the items to be tested undergo chemical reactions, that is have changes in properties, they cannot be subjected to pool testing, such as the testing of pH values.

(4) If the focus is on whether the items to be tested of the sample are detected, the report limit of the items to be tested of a single sample should be higher than the method detection limit.

(5) If the focus is on whether the items to be tested of the sample are qualified, the quantity limit should be higher than the report limit of a single sample.

2. The pooled-sample testing model can be used after the aforesaid conditions are all met.

(1) The expanded uncertainty of the item is calculated, and the safety factor is determined.

(2) The maximum number $K_{max}$ of samples that can be pooled is calculated using the mathematical model formula (4).

(3) The table is queried based on the positive rate/unqualified rate of the test item, and a number of samples that can be pooled, which reduces workload most greatly, is selected from 2 to $K_{max}$ as an optimum number of samples that can be pooled.

(4) After testing the pooled sample, the maximum content of certain substance to be tested for a single test sample is calculated, and then compared with the corrected report limit or quantity limit to determine whether the pooled sample is split for separate retesting.

The mathematical model established by the present invention, when conducting the chemical inspection and testing for consumer products, can scientifically and quickly determine whether the pool testing is available for the item and can scientifically calculate the maximum number of samples that can be pooled. By using the pooled-sample testing method, the number of tests in chemical analysis can be reduced, which can achieve the purposes of reducing workload and improving efficiency. In addition, the use of reagents can be reduced, such that emissions to the environment, the cost for handling large amounts of reagents and the cost of testing can all be reduced, thereby having obvious economic and social benefits for both the company and the country.

Figure 2:
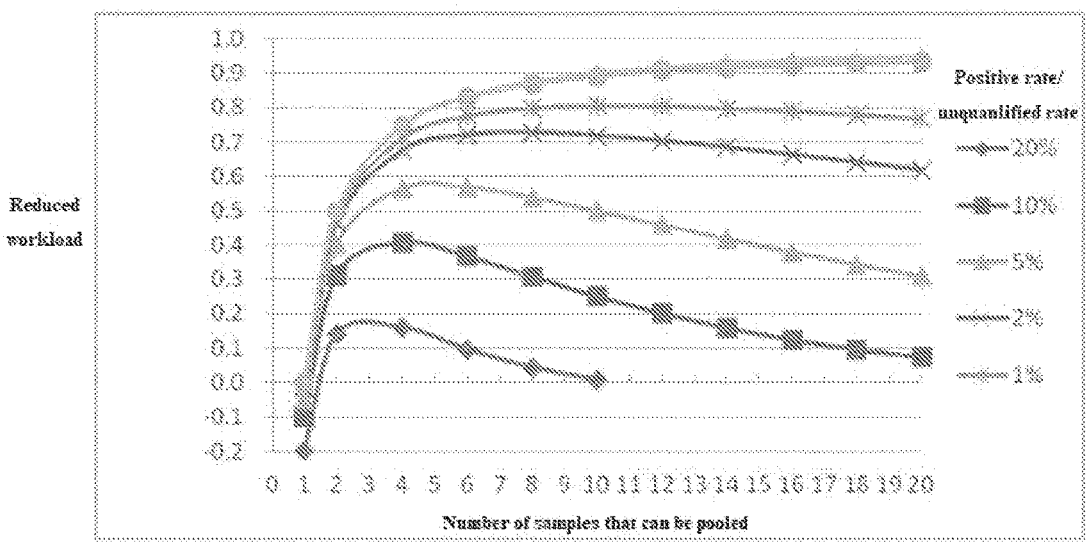
FIG. 2 is a statistical diagram of an optimization model for a classical scheme of a sample pooling method for once.

As mentioned above in formula (2)

$$N = n\left(1 - q^K + \frac{1}{K}\right) < n$$

and formula (3) reduced workload $$S = q^K - \frac{1}{K} > 0,$$

when the negative or qualified probability q is 100% (i.e., the positive or unqualified probability p is 0), the workload can be reduced if the number K of samples that can be pooled is greater than 1. That is, the workload can be reduced regardless of the number of samples as pooled. In this case, if K=2, S=0.5, reducing half of the workload; and if K=4, S=0.75, reducing three-quarters of the workload. The reduced workload corresponding to various positive probabilities p and the numbers K of samples that can be pooled are shown in Table 2 and FIG. 2.

TABLE 2

Workload saving efficiency table corresponding to positive rate or unqualified rate and pooled number

| Positive probabilities or unqualified probabilities P | Value of numbers K of samples that can be pooled | | | | | | | | |
|---|---|---|---|---|---|---|---|---|---|
| | 2 | 3 | 4 | 5 | 6 | 7 | 8 | 9 | 10 |
| 0.000 | 0.50[1] | 0.67 | 0.75 | 0.80 | 0.83 | 0.86 | 0.88 | 0.89 | 0.90 |
| 0.001 | 0.50 | 0.66 | 0.75 | 0.79 | 0.83 | 0.85 | 0.87 | 0.88 | 0.89 |
| 0.005 | 0.49 | 0.65 | 0.73 | 0.77 | 0.80 | 0.82 | 0.84 | 0.85 | 0.85 |
| 0.010 | 0.48 | 0.64 | 0.71 | 0.75 | 0.77 | 0.79 | 0.80 | 0.80 | 0.80 |
| 0.05 | 0.40 | 0.52 | 0.56 | 0.57[2] | 0.56 | 0.55 | 0.54 | 0.52 | 0.50 |
| 0.10 | 0.31 | 0.40 | 0.41[3] | 0.39 | 0.36 | 0.33 | 0.30 | 0.28 | 0.25 |
| 0.15 | 0.22 | 0.28 | 0.27 | 0.24 | 0.21 | 0.18 | 0.15 | 0.12 | 0.10 |
| 0.20 | 0.14 | 0.18 | 0.16 | 0.13 | 0.09 | 0.07 | 0.04 | 0.02 | 0.01 |
| 0.25 | 0.06 | 0.09 | 0.07 | 0.04 | 0.01 | −0.01 | −0.02 | −0.04 | −0.04 |
| 0.30 | −0.01 | 0.01[4] | −0.01 | −0.03 | −0.05 | −0.06 | −0.07 | −0.07 | −0.07[4] |
| 0.31[5] | −0.02 | −0.01 | −0.02 | −0.04 | −0.06 | −0.07 | −0.07 | −0.08 | −0.08 |

[1]When the positive or unqualified rate p = 0 (i.e., no substance detected or all qualified) and the number K of samples that can be pooled is 2, S equals to 0.5, thereby reducing half of the workload. The optimum number of samples that can be pooled is to pool all of the samples to perform only one test.

[2]When the positive or unqualified rate p is 0.05 (i.e., 5%) and the number K of samples that can be pooled is 5, the pool testing method reduces 57% of workload compared with the method that the samples are tested one by one. In this case, K, being 5, is the maximum value among all numbers of samples that can be pooled and the highest efficiency is achieved.

[3]If the positive rate or unqualified p = 0.10 (i.e., 10%), the highest efficiency is achieved when 4 samples are pooled.

[4]When the positive or unqualified rate increases to p = 0.30 (i.e., 30%), the highest efficiency can only be achieved by pooling three samples, but only 1% of the workload can be reduced. In this case, if 10 samples are pooled, the workload may even increase by 7%.

[5]If the positive rate further increases, the purpose of reducing workload cannot be achieved no matter how the pooling is performed.

Thus, it can be seen from Table 2 that the purpose of reducing workload can be achieved as long as the samples are scientifically pooled.

Below are two specific embodiments to further explain the quantitative pooled-sample testing method and apparatus for chemical test items of consumer products according to the present invention.

Embodiment 1. Pooled-Sample Testing for Phthalate Ester Items in Toys

The national toy safety standard GB 6675.1-2014 stipulates that the total content of three phthalate esters (DBP, BBP, DEHP) in toys must not be greater than 1000 mg/kg, tested in accordance with GB/T 22048-2015 Determination of Certain Phthalate Esters in Toys and Children's Products. By analyzing the unqualified rate, report limit and quantity limit of the test item, it is determined that a pooled-sample testing model is available, the procedure of which is as follows.

1. Testing Procedure

2. Testing Procedure as Shown in FIG. 4 Mathematical Model

The content of various phthalate ester plasticizer components in the samples is calculated according to the following formula:

$$X_i = (A_i \times C_s \times V_i)/(A_s \times m),$$

where $X_i$ refers to the content of the component to be tested in the sample in %;

$A_i$ refers to a peak area of the component to be tested in the sample;

$C_s$ refers to a concentration of the standard solution in mg/L;

V refers to a final volume-metered volume of the sample in ml;

$A_s$ refers to a peak area of the component to be tested in the standard solution; and m refers to a sample mass in g.

3. Sources of Standard Uncertainty

| Source | Evaluating method |
|---|---|
| Sample mass | Citing scale measurement uncertainty |
| Volume | Citing capacity uncertainty of capacity instruments/ volume uncertainty of liquid feeder |
| Reference material | Citing relative standard uncertainty of certificates |
| Deviation (recovery rate) | CRM samples and measurement uncertainty of spiked recovery rate |
| Precision | Based on parallel tests of different samples |

4. Calculation of Standard Uncertainty of Component 4.1 Relative Uncertainty of Sample Mass in u (m)/m According to the evaluation of the scale measurement uncertainty (UE-CW1), it can be seen that the measurement uncertainty at 1 g for mass measurement is 0.00064 g. Therefore, when m=1 g, u (m)/m=0.00064 g/1 g=0.00064.

4.2 Relative Uncertainty of Volume in u (V)/V

The maximum allowable error of a 25 mL A-Grade volumetric flask is 0.12%. It is assumed as triangular distribution, u (V)/V=0.0012/√6=0.00049 (Method B).

reference material; $S_{obs}$ refers to the standard deviation of the measured values; and n refers to the number of measurements.

Method B:

| Serial number | $C_{CRM}$ | Measurement 1 | Measurement 2 | Measurement 3 | Measurement 4 | Measurement 5 | Measurement 6 | Measurement 7 | $C_{obs}$ | $S_{obs}$ | $\overline{R_m}$ | t | $u(R_m)$ |
|---|---|---|---|---|---|---|---|---|---|---|---|---|---|
| DBP | 1109 | 1171 | 1201 | 1123 | 1227 | 1229 | 1265 | 1138 | 1193 | 52 | 1.08 | 0.70 | 0.016 |
| BBP | 1076 | 945 | 1069 | 965 | 1051 | 1020 | 1062 | 932 | 1006 | 58 | 0.94 | 0.67 | 0.022 |
| DEHP | 980 | 909 | 1045 | 906 | 1009 | 959 | 1111 | 894 | 976 | 82 | 1.00 | 0.04 | 0.032 |

4.3 Relative Uncertainty of Reference Materials in u (STD)

Steps: weighing approximately 0.02 g of certified reference material, and diluting the certified reference material to a volume of 100 mL (having a concentration of 200 mg/L); then, transferring 10 mL, 2.5 mL, 1.25 mL, 0.25 mL, and 0.1 mL of the diluted certified reference material and diluting them to a volume of 50 mL (having concentrations of 40 mg/L, 10 mg/L, 5 mg/L, 1 mg/L and 0.4 mg/L) respectively.

As found in the certificate of the standard phthalate ester plasticizer, the maximum uncertainty of the standard phthalate ester plasticizer is 5%. Then, the relative standard uncertainty in case of the uniform distribution can be obtained as 5%/√3=2.9%.

By querying the uncertainty procedure of the scale, when something is weighed about 0.02 g through the scale, the relative standard uncertainty is 0.00064 g/0.02 g=3.2%.

The relative standard uncertainty of 50 mL A-Grade volumetric flask is 0.1%.

As queried, the maximum relative standard uncertainty of the pipette gun is 3%.

Therefore, the maximum relative standard uncertainty of the standard working solution is:)

As found in the table, $t_{0.05,6}$ ($t_{0.05,6}$=2.45), and values oft in the table are all less than 2.45, which indicates that the recovery rate is not significantly different from 100%. Thus, there is no need to correct the results with the recovery rate while calculating the results.

4.4.2 Calculation of the Standard Deviation of Spiked Samples: $u(R_s)$

A series of representative samples of PU, coating, textile and liquid are taken respectively, and added with two standard concentrations of spiked 1 and spiked 2 (adding 0.5 mL of and 5 mL of 200 mg/L standard stock solution respectively, with the spiked concentrations being 4 mg/L and 40 mg/L respectively, which are equivalent to having sample concentrations of 100 mg/kg and 1000 mg/kg). Then, the series of representative samples are tested in parallel 7 times, and the recovery rates (in %) as calculated are shown in the following table.

$$u(R_s) = S_{std}/\sqrt{n},$$

Where $S_{std}$ refers to the standard deviation of the spiked recovery rate; and n refers to the number of spiked measurements (n=7 for this measurement)

| Serial number | PU with spiked 1 | PU with spiked 2 | Coating with spiked 1 | Coating with spiked 2 | Textile with spiked 1 | Textile with spiked 2 | Liquid with spiked 1 | Liquid with spiked 2 | $S_{std}$ | $u(R_s)$ |
|---|---|---|---|---|---|---|---|---|---|---|
| DBP | 0.99 | 0.95 | 0.99 | 0.96 | 1.09 | 1.02 | 0.88 | 1.08 | 0.05 | 0.019 |
| BBP | 0.94 | 0.96 | 1.00 | 1.03 | 0.91 | 0.98 | 0.90 | 0.95 | 0.04 | 0.016 |
| DEHP | 0.95 | 1.03 | 1.14 | 0.94 | 1.10 | 0.95 | 0.83 | 0.90 | 0.09 | 0.32 |

$$\sqrt{2.9\%^2 + 3.2\%^2 + 0.1\%^2 + 3\%^2} = 0.053$$

4.4 Relative Standard Uncertainty of Recovery Rate u (R)

4.4.1 Calculation of CRM Standard Deviation: $u(\overline{R_m})$

Certified reference material RMC010 blue PVC is taken and measured in parallel 7 times according to the procedure. The measurement results are as follows (in mg/kg):

$$u * \overline{R_m})s_{obs}/\sqrt{n}$$

$$\overline{R_m} = C_{obs}/C_{CRM}$$

$$t = \left|1 - \overline{R_m}\right|/u(\overline{R_m}),$$

Where $C_{obs}$ refers to the average value of the measured values; $C_{CRM}$ refers to the standard value of the certified 4.4.3 Calculation of u ($R_{rep}$)

For the measurement of phthalate esters with a solvent extracting method, the entire matrix is completely extracted. Thus, the spiked substance has no significant difference from the matrix and thus can be ignored.

4.4.4 Calculation of Relative Standard Uncertainty of Recovery Rate $$u(R) = \sqrt{\left[u(\overline{R_m})^2 + u(R_s)^2 + u(R_{rep})^2\right]}$$

| Serial number | $u(\overline{R_m})$ | $u(R_s)$ | $u(R)$ |
|---|---|---|---|
| DBP | 0.016 | 0.019 | 0.025 |
| BBP | 0.022 | 0.016 | 0.027 |
| DEHP | 0.032 | 0.032 | 0.045 |

4.5 Relative Standard Uncertainty of Precision: u (RSD)

A series of parallel tests are conducted on different types of samples on different dates to acquire a total random variation (precision) of the procedure. The testing results are shown in the table below, where 10 refers to CRM RMC010 blue PVC in mg/kg.

6. Calculation of Expanded Uncertainty

The calculation results of the relative standard uncertainty components are listed in the following table.

Combined uncertainty:

$$U(R) = \text{standard deviation}/\sqrt{2}$$

$$u(C_{sam})/C_{sam} = \sqrt{\left[u(m)/m\right]^2 + \left[u(V)/V\right]^2 + u(STD)^2 + u(R)^2 + u(RSD)\right]^2}.$$

DBP

| Serial number | Material | D1 | D2 | Average value | D1 − D2 | (D1 − D2)/average value |
|---|---|---|---|---|---|---|
| 1 | Orange plastic granules | 2250 | 2200 | 2225 | 50 | 0.022 |
| 2 | Green cloth | 900 | 870 | 885 | 30 | 0.034 |
| 3 | White coating on the plastic | 2000 | 1980 | 1990 | 20 | 0.010 |
| 4 | Black soft rubber | 1180 | 1140 | 1160 | 40 | 0.034 |
| 5 | Mixed coating on paper | 750 | 760 | 755 | −10 | −0.013 |
| 6 | Blue wire coat | 550 | 640 | 595 | −90 | −0.151 |
| 7 | White sticker | 460 | 450 | 455 | 10 | 0.022 |
| 8 | Red cloth with red thin layer | 550 | 570 | 560 | −20 | −0.036 |
| 9 | Mixed coating | 110 | 120 | 115 | −10 | −0.087 |
| 10 | Blue PVC | 1171 | 1201 | 1186 | −30 | −0.025 |
| | S.D. | | | | | 0.060 |
| | u(RSD) | | | | | 0.042 |

BBP

| Serial number | Material | D1 | D2 | Average Value | D1 − D2 | (D1 − D2)/average Value |
|---|---|---|---|---|---|---|
| 1 | Orange plastic granules | 1890 | 1830 | 1860 | 60 | 0.032 |
| 2 | Light green coating | 380 | 410 | 395 | −30 | −0.076 |
| 3 | Green soft rubber | 310 | 290 | 300 | 20 | 0.067 |
| 4 | Blue coating | 490 | 590 | 540 | −100 | −0.185 |
| 5 | Light purple coating on wood with white background | 230 | 210 | 220 | 20 | 0.091 |
| 6 | Red coating on wood with white background | 650 | 670 | 660 | −20 | −0.030 |
| 7 | Dark purple coating on wood | 970 | 1050 | 1010 | −80 | −0.079 |
| 8 | Green coating on wood with white background | 480 | 490 | 485 | −10 | −0.021 |
| 9 | Cream-colored soft rubber | 3700 | 3300 | 3500 | 400 | 0.114 |
| 10 | Blue PVC | 945 | 1069 | 1007 | −124 | −0.123 |
| | S.D. | | | | | 0.097 |
| | u(RSD) | | | | | 0.069 |

DEHP

| Serial number | Material | D1 | D2 | Average Value | D1 − D2 | (D1 − D2)/average Value |
|---|---|---|---|---|---|---|
| 1 | Orange plastic granules | 1350 | 1300 | 1325 | 50 | 0.038 |
| 2 | Black artificial leather | 160 | 170 | 165 | −10 | −0.061 |
| 3 | Black painting | 2200 | 2100 | 2150 | 100 | 0.047 |
| 4 | Sticker with coating | 430 | 360 | 395 | 70 | 0.177 |
| 5 | Mixed coating | 150 | 140 | 145 | 10 | 0.069 |
| 6 | Black soft rubber | 280 | 280 | 280 | 0 | 0.000 |
| 7 | Transparent plastic sheet | 14700 | 13800 | 14250 | 900 | 0.063 |
| 8 | Brown PCB | 570 | 610 | 590 | −40 | −0.068 |
| 9 | Black wire cover | 620 | 670 | 645 | −50 | −0.078 |
| 10 | Blue PVC | 909 | 1045 | 977 | −136 | −0.139 |
| | S.D. | | | | | 0.093 |
| | u(RSD) | | | | | 0.065 |

17

18

Expanded uncertainty:

$$U(C_{sam}) = k*[u(C_{sam})/C_{sam}].$$

The aforesaid components are combined by taking the coverage factor k of 2, and the calculation results are listed in the following table.

Combined Relative Standard Uncertainty

| Plasti-cizer | u (m)/m | u (V)/V | u (STD) | u (R) | u (RSD) | u $(C_{sam})/C_{sam}$ | u $(C_{sam})$ |
|---|---|---|---|---|---|---|---|
| DBP | 0.064 | 0.049 | 5.3 | 2.5 | 4.2 | 7.2 | 10.5 |
| BBP | 0.064 | 0.049 | 5.3 | 2.7 | 6.9 | 9.1 | 11.2 |
| DEHP | 0.064 | 0.049 | 5.3 | 4.5 | 6.5 | 9.6 | 12.1 |

The expanded uncertainty of the item is calculated. Assuming that the relative expanded uncertainties of DBP, BBP and DEHP are evaluated as 11%, 12%, and 12% respectively, the relative expanded uncertainty of DBP+BBP+DEHP can be calculated according to formula 5 as 20%.

According to formula 4 and the calculated expanded uncertainty, the maximum value $K_{max}$ of the number of samples that can be pooled is calculated as 17, which means that the maximum number of samples that can be pooled is 17. The unqualified rate of phthalate ester plasticizers in tens of thousands of toys and children's products is 0.5% according to statistic. According to Table 2, among the number of samples that can be pooled of 2 to 17, the number of samples that can be pooled, which reduces workload most greatly is 15, which can reduce 80% of the workload. Thus, the optimum number of samples that can be pooled is 15. In this case, the method detection limit for one phthalate ester in a single sample is 187 mg/kg, and the method detection limit for the sum of three phthalate esters in a single sample is 560 mg/kg.

It is assumed that the 15 samples subjected to pool testing are green PVC, red ABS, blue PU, . . . , and gray PVC, which have the mass of 0.0671 g, 0.0679 g, 0.0674 g, . . . , and 0.0679 g respectively, and the DEHP testing result after dilution to a volume of 25 ml is 1.6 mg/L. Then, the average content of DEHP in the pooled sample is as follows:

$$W_{avg} = \frac{1.6 \times 25}{0.0671 + 0.0679 + 0.0674 + \cdots + 0.0679} = \frac{1.6 \times 25}{1.0001} = 40 \text{ mg/kg}.$$

The maximum DEHP content in a single sample is as follows:

$$W_{max} = \frac{1.6 \times 25}{0.0671} = 596 \text{ mg/kg}.$$

Due to the similar mass of the 15 samples, the maximum DEHP content can also be calculated as follows:

$$W_{max} = W_{avg} \times = 40 \times 15 = 600 \text{ mg/kg}.$$

Because the relative expanded uncertainty $U_{rel}$ around the limit concentration is 20% and the safety factor F is 80%, the corrected quantity limit is as follows:

$$L' = L \times (1 - U_{Rel}) \times F = 1000 \times (1 - 20\%)80\% = 620 \text{ mg/kg}.$$

Because the quantity limit is the sum of three test items, how to calculate the content of other undetected items is also involved. Different conclusions may be made under different calculation methods (including the calculation by 0, calculation by half of the method detection limit, and calculation by the method detection limit). The report results are shown in Table 4:

TABLE 4

| Phthalate ester detection report | | | | | |
|---|---|---|---|---|---|
| Samples subjected to pool testing | Test items | Quantity limit (mg/kg) | Method detection limit (mg/kg) for single sample | Maximum content of single sample (mg/kg) | Conclusion |
| 15 pooled | DBP | — | 187 | ≤187 | — |
| samples such as | BBP | — | 187 | ≤187 | — |
| Green PVC/ | DEHP | — | 187 | 600 | — |
| Red ABS/ | DBP + BBP + | 1000 | 560 | =600[1] | Qualified [4] |
| Blue PU/ . . . / | DEHP | | | =787[2] | Requiring splitting [5] |
| Grey PVC | | | | ≤974[3] | Requiring splitting [5] |

[1]The calculation is performed by taking the content of DBP and BBP as equal to 0.
[2]The calculation is performed by taking the content of DBP and BBP as half of the method detection limit.
[3]The calculation is performed by taking the content of DBP and BBP as less than or equal to the method detection limit.
[4] 600 mg/kg is less than the corrected quantity limit of 640 mg/kg.
[5] 787 mg/kg and 974 mg/kg are greater than the corrected quantity limit of 640 mg/kg.

Embodiment 2. Pooled-Sample Testing for Content of Banned Aromatic Amines in Textiles Testing the content of banned aromatic amines in textiles is one of the most important quality monitoring items in international textile and clothing trade, and also one of the most basic quality indicators for ecological textiles. The German government issued a decree in 1994 stipulating that all leather and textiles entering Germany must undergo the testing of banned aromatic amines. Then, other countries around the world and OEKO-TEX® (International Environmental Textile Association) has followed suit. Therefore, the workload of testing banned aromatic amines in textiles by global testing organizations is very heavy, and thus it is very necessary to perform the pooled-sample testing.

When testing 22 banned aromatic amines in textiles according to ISO 14362-1:2017, if the report limit for a single banned aromatic amine is chosen as 5 mg/kg, $U_{rel}$ is 0% (because no quantity limit is involved, no uncertainty needs to be considered) and the safety factor F is 90%, the testing may be performed according to this method, 1 g of test items is weighed and finally diluted to a volume of 2 ml ($m_{tot}$=1 g, V=2 ml), and the detection limit IDL as tested with a high performance liquid chromatography-mass spectrometer (HPLC-MS/MS) of A.3.2 is 0.1 mg/L (the least sensitive aromatic amine in terms of detection limit). Because the report limit is for each aromatic amine (not the sum of 22 aromatic amines), the number M of test item is 1, and the maximum number of samples that can be pooled is calculated as $K_{max}$=22. That is, a maximum of 22 samples can be pooled. As learned from the agency statistics, the positive detection rate of banned aromatic amines in textiles is 5% (for most of them, aniline, a breakdown product of 4-aminoazobenzene is detected, and thus additional testing is required to determine whether 4-aminoazobenzene is actually contained). By querying Table 2, among the number of samples that can be pooled of 2 to 22, the number of samples that can be pooled, which reduces workload most greatly is 5, which can reduce 57% of the workload. Thus, the optimum number of samples that can be pooled is 5. The method detection limit (MDL) of one aromatic amine in pooled samples is 0.2 mg/kg (based on the total mass of the pooled samples), and if the method detection limit of a single sample is to be reported, the MDL is 5 times MDL of one aromatic amine in pooled samples. Thus, the method detection limit of one aromatic amine in a single sample is 1 mg/kg, which fully meets requirement of the report limit of 5 mg/kg.

It is assumed that the 5 samples subjected to pool testing include red cloth, green cloth, blue cloth, yellow cloth and purple cloth, which have the mass of 0.2000 g, 0.2005 g, 0.2004 g, 0.1998 g and 0.1996 g respectively. In addition, the testing result of benzidine after dilution to a volume of 2 ml is 0.41 mg/L. Then, the average content of benzidine in the pooled samples is as follows:

$$W_{avg} = \frac{0.41 \times 2}{0.2000 + 0.2005 + 0.2004 + 0.1998 + 0.1996} = \frac{0.41 \times 2}{1.0003} = 0.82 \text{ mg/kg.}$$

The maximum content of benzidine in a single sample is as follows:

$$W_{max} = \frac{0.41 \times 2}{0.1996} = 4.1 \text{ mg/kg.}$$

Since the mass of the five samples is similar, the maximum content can also be calculated as follows:

$$W_{max} =$$

$$W_{avg} \times \text{the number of samples that can be pooled} = 0.82 \times 5 = 4.1 \text{ mg/kg.}$$

Since $U_{rel}$=0% (since no quantity limit is involved, no uncertainty needs to be considered) and the safety factor F=90%, the corrected quantity limit is as follows:

$$L' = L \times (1 - U_{rel}) \times F = 5 \times (1 - 0\%) \times 90\% = 4.5 \text{ mg/kg.}$$

Their report results are shown in Table 5:

TABLE 5

| Test report of aromatic amines | | | | | |
|---|---|---|---|---|---|
| Samples subjected to pool testing | Test items | Report limit (mg/kg) | Method detection limit (mg/kg) for a single sample | Maximum content in a single sample (mg/kg) | Conclusion |
| 5 samples in total: | 4-aminobiphenyl | 5 | 1 | ≤1 | |
| red cloth/green | Benzidine | 5 | 1 | 4.1 | Requiring no splitting |
| cloth/blue | | | | | |
| cloth/yellow | 4-chloro-o-toluidine | 5 | 1 | ≤1 | — |
| cloth/purple cloth | 2-naphthylamine | 5 | 1 | ≤1 | — |
| | o-aminoazotoluene | 5 | 1 | ≤1 | |
| | 5-nitro-o-toluidine | 5 | 1 | ≤1 | |
| | p-chloroaniline | 5 | 1 | ≤1 | — |
| | 2,4-diaminoanisole | 5 | 1 | ≤1 | — |
| | 4,4'-diaminodiphenylmethane | 5 | 1 | ≤1 | |
| | 3,3'-dichlorobenzidine | 5 | 1 | ≤1 | |
| | 3,3'-dimethoxybenzidine | 5 | 1 | ≤1 | — |
| | 3,3'-dimethylbenzidine | 5 | 1 | ≤1 | |
| | 3,3'-dimethyl-4,4'-diaminodiphenylmethane | 5 | 1 | ≤1 | |
| | 2-methoxy-5-methylaniline | 5 | 1 | ≤1 | — |
| | 4,4'-methylene-bis-(2-chloroaniline) | 5 | 1 | ≤1 | — |
| | 4,4'-diaminodiphenyl ether | 5 | 1 | ≤1 | |
| | 4,4'-diaminodiphenyl sulfide | 5 | 1 | ≤1 | |
| | o-toluidine | 5 | 1 | ≤1 | — |
| | 2,4-diaminotoluene | 5 | 1 | ≤1 | — |
| | 2,4,5-trimethylaniline | 5 | 1 | ≤1 | |
| | 2-methoxyaniline | 5 | 1 | ≤1 | |
| | 4-aminoazobenzene | 5 | 1 | ≤1 | |

4.1 mg/kg is less than the corrected report limit of 4.5 mg/kg.

Under the promotion of the applicant of the present invention, the concept of pooled-sample testing, empirical scheme and the like have been introduced into Appendix D of the international standard ISO 8124-6:2018 Certain Phthalate Esters in Toys and Children's Products (please refer to Annex 1 for details), which has been officially published and used, and adopted and well received by the majority of testing organizations. However, this version has no mathematical model and lacks mathematical quantitative analysis for properties of various chemical ingredients to be analyzed, chemical instrumentation capabilities, pretreatment techniques, and the like. For this reason, at the annual meeting of the International Standardization Organization/Technical Committee ISO/TC 181 on "Safety of Toys" held in Seoul, Korea in September 2019, after thorough discussions by countries, it was decided in Resolution 217 to introduce the content of the present invention in the next edition of ISO 8124. That is, the mathematical model of the pooled-sample testing was published as the official normative appendix of the international standard, with Lina HUANG (the applicant of the present invention) as the project leader. Meanwhile, In Resolution 218 of the meeting, it was decided to re-appoint Lina HUANG (the applicant of the present invention) as the convener of ISO/TC181/WG6 working group to undertake the task of revising ISO 8124-6 Certain Phthalate Esters in Toys and Children's Products, and the task is mainly to introduce the mathematical model of the pooled-sample testing of the present invention (please refer to Annex 2 for details). This is a milestone for China to occupy the strategic high point of international standards, and also indirectly reflects that the present invention possesses inventiveness.

The aforesaid embodiments are only for explaining implementation manners of the present invention in a relatively specific and detailed description manner, but they shall not be understood as a limitation on the scope of the invention patent. It shall be pointed out that a person of ordinary skill in the art may further make several modifications and improvements without departing from the concept of the present invention, and the modifications and improvements shall fall within the protection scope of the present application. Therefore, the protection scope of the invention patent shall be subject to the appended claims.

What is claimed is:

1. A quantitative pooled-sample testing method for chemical test items of consumer products, comprising steps of:

acquiring relevant data of an item to be tested, and entering the relevant data into the following model to calculate a maximum number of samples allowed to be pooled:

$$K_{max} = L \times (1 - U_{rel}) \times F \times \frac{m_{tot}}{V} \div IDL \div M,$$

where $K_{max}$ refers to the maximum number of samples allowed to be pooled, $K_{max}$ is rounded by removing a mantissa; L refers to a quantity limit or report limit of the item to be tested and is in mg/kg; $U_{rel}$ refers to a relative expanded uncertainty around a limit concentration;

F refers to a safety factor of the quantity limit or report limit; $m_{tot}$ refers to a total mass of samples subjected to pool testing and is in g; V refers to a volume of a volume-metered solution and is in mL; IDL refers to an instrument detection limit and is in mg/L; M refers to a number of the items to be tested corresponding to the quantity limit or report limit;

if the quantity limit is only one chemical test item, calculating the $U_{rel}$ according to the following formula:

$$U_{rel} = u_{rel} \times k$$

$$u = \sqrt{u_{rel,1}^2 + u_{rel,2}^2 + u_{rel,3}^2},$$

where $u_{rel}$ refers to a relative standard uncertainty around the limit concentration; k refers to a coverage factor taken with a confidence level of 95%, and k=2; $u_{rel,1}$ refers to a relative standard uncertainty of method reproducibility, wherein $u_{rel,1}$ is namely a standard deviation of reproducibility data; $U_{rel,2}$ refers to a relative standard uncertainty of a method recovery rate; and $u_{rel,3}$ refers to a relative standard uncertainty of a standard curve;

if the quantity limit is a sum of a plurality of chemical test items, calculating the $U_{rel}$ according to the following formula:

$$U_{rel} = u \div L \times k$$

$$u = \sqrt{u_1^2 + u_2^2 + u_3^2 + \ldots + u_n^2},$$

where u refers to a standard uncertainty around the limit concentration and is in mg/L; L refers to the quantity limit or report limit of the item to be tested and is in mg/kg; k refers to the coverage factor taken with the confidence level of 95% and k=2; $u_1$ refers to a standard uncertainty of an item 1 to be tested and is in mg/kg; $u_2$ refers to a standard uncertainty of an item 2 to be tested and is in mg/kg; and us refers to a standard uncertainty of an item 3 to be tested and is in mg/kg;

determining a positive rate or unqualified rate of the item to be tested, querying a workload-reducing efficiency table to select a number of samples allowed to be pooled, wherein the number of samples allowed to be pooled reduces workload most greatly, among 2 to $K_{max}$ as an optimum number of samples allowed to be pooled, wherein the workload-reducing efficiency table is established according to the following formula:

$$S = q^K - \frac{1}{K},$$

where S refers to a reduced workload, q refers to the positive rate or unqualified rate, and K refers to the number of samples allowed to be pooled; and grouping samples to be tested according to the optimum number of samples allowed to be pooled, and performing a pooled-sample chemical testing for plasticizers in a consumer product with reagents on at most the grouped samples to measure plasticizer content in the consumer product with at most a 5% uncertainty.

2. The quantitative pooled-sample testing method according to claim 1, wherein after the pooled-sample testing, a maximum content of a substance to be tested in a single test sample is calculated; and if the maximum content exceeds a corrected quantity limit or report limit, the pooled sample is split and the samples are tested separately.

3. The quantitative pooled-sample testing method according to claim 1, wherein the positive rate/unqualified rate of the items to be tested is less than 20%.

4. The quantitative pooled-sample testing method according to claim 1, wherein the safety factor F of the quantity limit or report limit is self-determined by respective testing laboratories, ranges from 0% to 100% and is related to respective testing levels of the laboratories.

5. A quantitative pooled-sample testing apparatus for chemical test items of consumer products, comprising:

a module for calculating a maximum number of samples allowed to be pooled, configured to: acquire relevant data of an item to be tested and enter the relevant data into the following model to calculate the maximum number of samples allowed to be pooled:

$$K_{max} = L \times (1 - U_{rel}) \times F \times \frac{m_{tot}}{V} \div IDL \div M,$$

where $K_{max}$ refers to the maximum number of samples allowed to be pooled, $K_{max}$ is rounded by removing a mantissa; L refers to a quantity limit or report limit of the item to be tested and is in mg/kg; $U_{rel}$ refers to a relative expanded uncertainty around a limit concentration; F refers to a safety factor of the quantity limit or report limit; mtt refers to a total mass of samples subjected to pool testing and is in g; V refers to a volume of a volume-metered solution and is in mL; IDL refers to an instrument detection limit and is in mg/L; M refers to a number of the items to be tested corresponding to the quantity limit or report limit;

if the quantity limit is only one chemical test item, the $U_{rel}$ is calculated according to the following formula:

$$U_{rel} = u_{rel} \times k$$

$$u = \sqrt{u_{rel,1}^2 + u_{rel,2}^2 + u_{rel,3}^2},$$

where $u_{rel}$ refers to a relative standard uncertainty around the limit concentration; k refers to a coverage factor taken with a confidence level of 95% and k=2; $u_{rel,1}$ refers to a relative standard uncertainty of method reproducibility, wherein $u_{rel,1}$ is namely a standard deviation of reproducibility data; $u_{rel,2}$ refers to a relative standard uncertainty of a method recovery rate; and $u_{rel,3}$ refers to a relative standard uncertainty of a standard curve, wherein $u_{rel,3}$ is namely a standard deviation of reproducibility data;

if the quantity limit is a sum of a plurality of chemical test items, the $U_{rel}$ is calculated according to the following formula:

$$U_{rel} = u \div L \times k$$

$$u = \sqrt{u_1^2 + u_2^2 + u_3^2 + \ldots + u_n^2},$$

where u refers to a standard uncertainty around the limit concentration and is in mg/L; L refers to the quantity limit or report limit of the item to be tested and is in mg/kg; k refers to the coverage factor taken with the confidence level of 95% and k=2; $u_1$ refers to a standard uncertainty of an item 1 to be tested and is in mg/kg; $u_2$ refers to a standard uncertainty of an item 2 to be tested and is in mg/kg; and $u_3$ refers to a standard uncertainty of an item 3 to be tested and is in mg/kg;

a module for determining an optimum number of samples allowed to be pooled, configured to: according to a positive rate or unqualified rate of the item to be tested, query a workload-reducing efficiency table to select a number of samples allowed to be pooled, the number of samples allowed to be pooled reduces workload mostly greatly, among 2 to $K_{max}$ as the optimum number of samples allowed to be pooled, wherein the workload-reducing efficiency table is established according to the following formula:

$$S = q^K - \frac{1}{K},$$

where S refers to a reduced workload, q refers to the positive rate or unqualified rate, and K refers to the number of samples allowed to be pooled; and a pooled-sample testing module, configured to group samples to be tested according to the optimum number of samples allowed to be pooled and perform a pooled-sample chemical testing for plasticizers in a consumer product with reagents on at most the grouped samples to measure plasticizer content in the consumer product with at most a 5% uncertainty.

6. The quantitative pooled-sample testing apparatus according to claim 5, wherein after performing the pooled-sample testing, the pooled-sample testing module calculates a maximum content of a substance to be tested in a single test sample, and if the maximum content exceeds a corrected quantity limit or report limit, splits the pooled sample and tests the samples separately.

7. The quantitative pooled-sample testing apparatus according to claim 5, wherein the positive rate/unqualified rate of the items to be tested is less than 20%.

8. The quantitative pooled-sample testing apparatus according to claim 5, wherein the safety factor F of the quantity limit or report limit ranges from 0% to 100% and is related to respective testing levels of laboratories.

9. The quantitative pooled-sample testing method according to claim 2, wherein the positive rate/unqualified rate of the items to be tested is less than 20%.

10. The quantitative pooled-sample testing method according to claim 2, wherein the safety factor F of the quantity limit or report limit is self-determined by respective testing laboratories, ranges from 0% to 100% and is related to respective testing levels of the laboratories.

11. The quantitative pooled-sample testing apparatus according to claim 6, wherein the positive rate/unqualified rate of the items to be tested is less than 20%.

12. The quantitative pooled-sample testing apparatus according to claim 6, wherein the safety factor F of the quantity limit or report limit ranges from 0% to 100% and is related to respective testing levels of laboratories.

\* \* \* \* \*